(12) United States Patent
Watson

(10) Patent No.: US 6,228,367 B1
(45) Date of Patent: May 8, 2001

(54) FOOD SUPPLEMENT FORMULATION

(75) Inventor: Tommy Stanley Watson, Tarpon Springs, FL (US)

(73) Assignee: Renew Life, Inc., Tarpon Springs, FL (US)

( * ) Notice: Subject to any disclaimer, the term of this patent is extended or adjusted under 35 U.S.C. 154(b) by 0 days.

(21) Appl. No.: 09/470,003

(22) Filed: Dec. 22, 1999

(51) Int. Cl.⁷ .......................... A61K 35/78; A61K 35/60
(52) U.S. Cl. .................. 424/195.1; 424/523; 424/554; 424/555; 426/585; 426/601; 426/615; 426/643
(58) Field of Search ................................ 424/523, 554, 424/555, 195.1; 435/134, 135; 426/585, 601, 615, 643

(56) References Cited

U.S. PATENT DOCUMENTS

| | | | | |
|---|---|---|---|---|
| 4,769,243 | * | 9/1988 | Kanisawa et al. | 426/33 |
| 4,792,418 | * | 12/1988 | Rubin et al. | 260/412 |
| 5,043,328 | * | 8/1991 | Weithmann | 514/78 |
| 5,681,608 | * | 10/1997 | Cain et al. | 426/606 |
| 5,962,712 | * | 10/1999 | DeMichele et al. | 554/224 |
| 6,077,828 | * | 1/2000 | Abbruzzese et al. | 514/21 |

* cited by examiner

*Primary Examiner*—James M. Spear
*Assistant Examiner*—Liliana Di Nola-Baron
(74) *Attorney, Agent, or Firm*—Donald R. Fraser

(57) ABSTRACT

A food supplement formulation comprises flaxseed oil, borage seed oil, fish oil, and lipase.

20 Claims, No Drawings

FOOD SUPPLEMENT FORMULATION

FIELD OF THE INVENTION

The present invention relates generally to a food supplement formulation. More particularly, the invention is directed to a food supplement formulation primarily containing essential fatty acids which are important for maintaining good health.

BACKGROUND OF THE INVENTION

Natural compounds and herbal formulations can provide a supplement to the daily human diet. Certain compounds are useful to the human body, but are not produced in substantial quantities thereby. Thus, natural formulations have been found to be useful for supplementing the intake of these compounds from the human diet.

It would be desirable to prepare a food supplement formulation which may be taken in excess of the daily human diet, which food supplement formulation may promote general health.

SUMMARY OF THE INVENTION

Accordant with the present invention, there surprisingly has been discovered a food supplement formulation, comprising:

flaxseed oil; borage seed oil; fish oil; and lipase.

The food supplement formulation according to the present invention is useful as a dietary supplement.

DETAILED DESCRIPTION OF THE PREFERRED EMBODIMENT

The present invention is directed to a food supplement formulation, comprising flaxseed oil, borage seed oil, fish oil, and lipase. The inventive formulation may be mixed together by conventional mixing equipment, and inserted, in dosage-sized quantities, into gelatin capsules for oral administration.

Flaxseed oil is a well-known compound containing omega-6 and omega-3 essential fatty acids in the forms of alpha-linolenic acid and linoleic acid. The body converts these fatty acids into other important fatty acids, which are used by the body for the production of prostaglandins. Prostaglandins are then used by the body to maintain healthy cholesterol and blood fat levels, support healthy blood pressure levels, and protect the membranes that surround the body's nerves.

Flaxseed oil may be present in the inventive food supplement formulation at a concentration from about 10 to about 60 weight percent. Preferably, the concentration is from about 20 to about 40 weight percent. Most preferably, the concentration of flaxseed oil is about 33.15 weight percent.

Borage seed oil is a well-known compound which contains a high concentration of the essential fatty acid gamma-linolenic acid. Gamma-linolenic acid is normally synthesized in the liver from dietary linoleic acid. The synthesis is deficient in a substantial number of people because of the interference by sugar, saturated fats, and trans-fatty acids. Gamma-linolenic acid is a precursor to the production of prostaglandins and other hormones in the body.

Borage seed oil may be present in the inventive food supplement formulation at a concentration from about 10 to about 60 weight percent. Preferably, the concentration is from about 20 to about 40 weight percent. Most preferably, the concentration of borage seed oil is about 33.15 weight percent.

Fish oil is a well-known compound which contains high concentrations of eicosapentaenoic acid and docosahexaenoic acid. These polyunsaturated long-chain fatty acids have been shown to assist in preventing cardiovascular disease, by reducing triglycerides and cholesterol in the blood stream, thinning the blood, and increasing the high-density lipoprotines in the body.

Fish oil may be present in the inventive food supplement formulation at a concentration from about 10 to about 60 weight percent. Preferably, the concentration is from about 20 to about 40 weight percent. Most preferably, the concentration of fish oil is about 33.15 weight percent.

Lipase is a well-known compound, consisting of enzymes that help the body's digestive system break-down and digest fats, cellulose, carbohydrates, and proteins. Lipase enzymes are produced by the body's liver and pancreas. In a substantial number of people, however, the production of lipase enzymes is deficient. Lipase from plants may be used to supplement the body's production.

Lipase may be present in the inventive food supplement formulation at a concentration from about 0.1 to about 2 weight percent. Preferably, the concentration is about 0.25 to about 1 weight percent. Most preferably, the concentration of lipase is about 0.55 weight percent.

The ingredients of the inventive food supplement formulation may synergistically work together to improve bodily functions such as, for example, cardiovascular function, joint flexibility, fat metabolism, nervous system and brain function, hormone production, and cell division.

Conveniently, the inventive food supplement formulation may be taken orally at a dosage rate ranging from about 200 milligrams per day to about 2,000 milligrams per day. Preferably, the dosage rate is about 1,000 milligrams per day. The prescribed dosage rates may be effective to supplement the lack of important compounds required by the body for promoting general health.

This invention is more easily comprehended by reference to the specific embodiments recited hereinabove which are representative of the invention. It must be understood, however, that the specific embodiments are provided only for the purpose of illustration, and that the invention may be practiced otherwise than as specifically illustrated without departing from its spirit and scope.

What is claimed is:

1. A food supplement formulation, consisting essentially of:

flaxseed oil;

borage seed oil;

fish oil; and lipase.

2. The food supplement formulation according to claim 1, wherein the concentration of flaxseed oil ranges from about 10 to about 60 weight percent.

3. The food supplement formulation according to claim 1, wherein the concentration of borage seed oil ranges from about 10 to about 60 weight percent.

4. The food supplement formulation according to claim 1, wherein the concentration of fish oil ranges from about 10 to about 60 weight percent.

5. The food supplement formulation according to claim 1, wherein the concentration of lipase ranges from about 0.1 to about 2 weight percent.

6. The food supplement formulation according to claim 2, wherein the concentration of flaxseed oil ranges from about 20 to about 40 weight percent.

7. The food supplement formulation according to claim 3, wherein the concentration of borage seed oil ranges from about 20 to about 40 weight percent.

8. The food supplement formulation according to claim 4, wherein the concentration of fish oil ranges from about 20 to about 40 weight percent.

9. The food supplement formulation according to claim 1, wherein the concentration of flaxseed oil is about 33.15 weight percent, the concentration of borage seed oil is about 33.15 weight percent, the concentration of fish oil is about 33.15 weight percent, and the concentration of lipase is about 0.55 weight percent.

10. A food supplement formulation, consisting essentially of:

from about 10 to about 60 weight percent flaxseed oil;
from about 10 to about 60 weight percent borage seed oil;
from about 10 to about 60 weight percent fish oil; and
from about 0.1 to about 2 weight percent lipase.

11. The food supplement formulation according to claim 10, wherein the concentration of flaxseed oil ranges from about 20 to about 40 weight percent.

12. The food supplement formulation according to claim 10, wherein the concentration of borage seed oil ranges from about 20 to about 40 weight percent.

13. The food supplement formulation according to claim 10, wherein the concentration of fish oil ranges from about 20 to about 40 weight percent.

14. The food supplement formulation according to claim 10, wherein the concentration of lipase ranges from about 0.25 to about 1 weight percent.

15. The food supplement formulation according to claim 11, wherein the concentration of flaxseed oil is about 33.15 weight percent.

16. The food supplement formulation according to claim 12, wherein the concentration of borage seed oil is about 33.15 weight percent.

17. The food supplement formulation according to claim 13, wherein the concentration of fish oil is about 33.15 weight percent.

18. The food supplement formulation according to claim 14, wherein the concentration of lipase is about 0.55 weight percent.

19. A food supplement formulation, consisting essentially of:

from about 20 to about 40 weight percent flaxseed
from about 20 to about 40 weight percent borage seed oil;
from about 20 to about 40 weight percent fish oil; and
from about 0.25 to about 1 weight percent lipase.

20. A food supplement formulation, consisting essentially of:

about 33.15 weight percent flaxseed oil;
about 33.15 weight percent borage seed oil;
about 33.15 weight percent fish oil; and
about 0.55 weight percent lipase.

* * * * *